United States Patent [19]

Monek

[11] Patent Number: 4,753,349

[45] Date of Patent: Jun. 28, 1988

[54] LABORATORY TEST KIT AND METHOD FOR PRESERVING LABORATORY SPECIMENS

[76] Inventor: Francis J. Monek, P.O. Box 769, Grayslake, Ill. 60030

[21] Appl. No.: 687,931

[22] Filed: Dec. 31, 1984

[51] Int. Cl.$^4$ ............................................. A61B 10/00
[52] U.S. Cl. .................................... 206/456; 206/592; 206/438; 435/296; 435/294; 435/810
[58] Field of Search ............... 206/456, 455, 592, 591, 206/438; 435/296, 294, 810

[56] References Cited

U.S. PATENT DOCUMENTS

| | | | |
|---|---|---|---|
| 3,643,650 | 2/1972 | Elder | 435/294 |
| 3,651,926 | 3/1972 | Elfast, Jr. | 435/296 |
| 3,843,452 | 10/1974 | Freake et al. | 435/294 |
| 3,849,256 | 11/1974 | Linder | 435/296 |
| 3,913,562 | 10/1975 | Moore et al. | 435/810 |
| 4,073,695 | 2/1978 | Lyman | 435/296 |
| 4,247,634 | 1/1981 | Abdou | 435/296 |
| 4,271,270 | 6/1981 | Lukacsek | 435/294 |

FOREIGN PATENT DOCUMENTS 2098626 5/1981 United Kingdom ................ 435/296

*Primary Examiner*—Joseph Man-Fu Moy
*Attorney, Agent, or Firm*—Martin Faier

[57] ABSTRACT

A laboratory test kit includes a container packed with an elongated foldable tray. The tray has legs elevating one portion of it to define a specimen receiving surface. The container houses other test paraphernalia, such as an ampule of fixative solution and utensils for taking a specimen and placing it on the tray specimen receiving surface. During specimen taking, the utensils and ampule may be carried on the tray ready and convenient for use. After the specimen is applied to the receiving surface and fixed as required, the tray legs may be bent in reverse direction and the tray may be folded and inserted into the container protecting the specimen for delivery to the laboratory.

28 Claims, 1 Drawing Sheet

U.S. Patent    Jun. 28, 1988    4,753,349
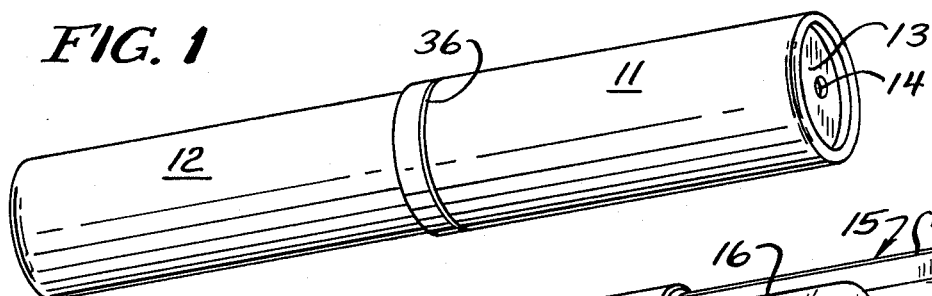
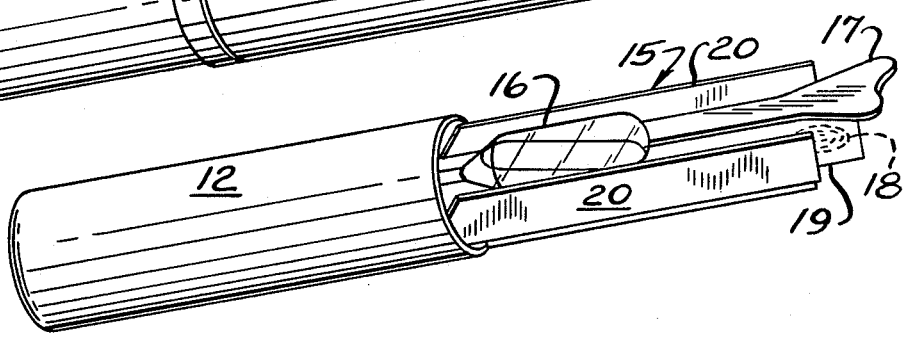
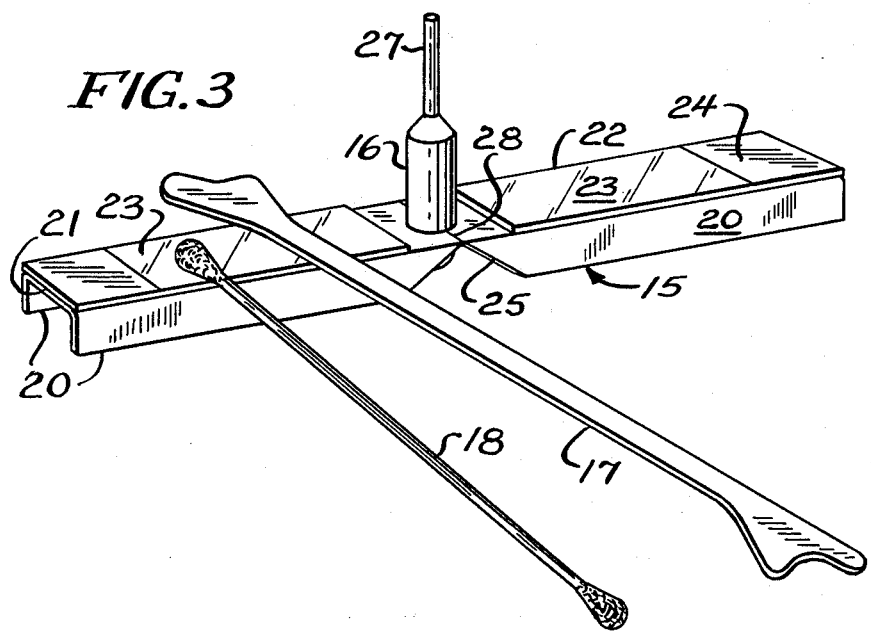
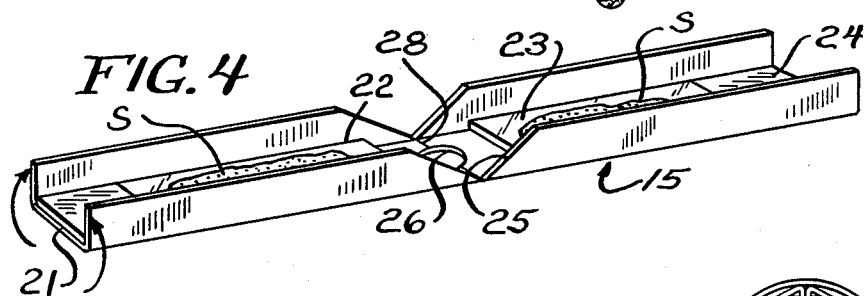

LABORATORY TEST KIT AND METHOD FOR PRESERVING LABORATORY SPECIMENS

BACKGROUND AND SUMMARY OF THE INVENTION

This invention relates to laboratory test kits and a method for preserving a laboratory specimen from the time it is taken until examined by a laboratory technician. The invention is particularly useful in securing and preserving gynecologic smears for laboratory testing.

Conventionally, a physician or technician, using a cervical scraper or similar instrument, takes a specimen from a patient and smears the specimen on to a transparent slide, after which the smear is covered by a fixative solution, and then transported to a laboratory for examination. Test kits which include a slide glued to a cardboard carrier are known in the art, and such kits have included containers for housing smeared slides during transport from the place of taking the specimen to the place of examination.

However, such conventional kits do not provide the novel slide holder design of the present invention. They have no means for holding the cytology ampule in an opened state ready for immediate use without spilling or evaporating. Applicant's novel slide carrier tray not only has means for presenting the specimen receiving surface in a convenient ready posture, but also the tray is folded in a novel predetermined manner and its legs are bent to protect the specimen. Additionally, the tray legs have an inverted V-shaped cut-out area which, when the tray is folded, provide an arrow-like leading edge which simplifies insertion of the specimen into the container for delivery to a place of examination. This folded slide carrier or tray is held by the bent legs in a flexible fashion, retained in position in the container, so that the specimen and slide are protected from shock during transit. The ends of the novel container have perforations, which permit air flow over the specimens to fully dry the smear fixative even after the container is closed, so the technician need not wait for complete drying or take a chance of specimen damage while waiting for complete drying.

Applicant's novel telescopic tube design allows the joined tubes to be extended for holding the carrier tray and utensils and other paraphernalia prior to use, but when telescoped one tube section into the other, the inner tube section functions to secure the loaded specimen tray remote from possibilities of damage. The double wall container design further protects the specimen during transport.

The design of applicant's test kit permits safe and easy storage of such kits prior to use and facilities convenient presentation of the contents of the kit to and use by the person taking the specimen. After the specimen is collected, the kit design prevents scratching or contamination of the specimen and inhibits breaking of or damage to the slide while being carried to the place of testing or examination.

Applicant's method for preserving the specimen using this novel kit is also unique and inventive, inasmuch as it includes the steps of applying a laboratory slide to a foldable carrier tray having bendable side legs positioned for elevating the slide surface during taking of a specimen, bending the carrier tray legs in a reverse direction to said elevating position and folding the tray after taking the specimen to dispose the slide surface outwardly on the tray, and inserting the folded and bent tray assembly into a tubular container so that the legs bear against the container wall to suspend the slide within the container. The method steps may also include providing an opaque surface behind the slide and a writing surface at one end of the slide for viewing the specimen area and for identifying the specimen, respectively, as well as closing the container with a telescopic tube for protecting the specimen during transport to a laboratory. Additionally, the process may include providing an ampule of solution and inserting the ampule in an aperture in the carrier tray during use, as well as drying the solution fully after the container is closed by means of perforations or ports in the end walls of the tubes which allow air circulation within the container.

OBJECTS AND ADVANTAGES OF THE INVENTION

It is the object of the invention to provide a laboratory test kit and a method for preserving laboratory specimen of the character described.

Another object is to provide a novel slide carrier or tray for a laboratory test kit.

Another object is to provide a novel slide carrier having secured thereon one or more laboratory slides which are adapted to receive a specimen on a surface thereof and have means for marking indicia thereon.

Another object is to provide an opaque background for a transparent slide secured on a slide carrier.

Another object is to provide an aperture in a slide carrier for holding an ampule of fixative solution.

Another object is to provide a slide carrier with parallel spaced apart bendable legs having a specimen receiving surface therebetween, which when bent in one direction elevates said surface for use and when bent in a reverse direction are adapted for insertion into a container to protect the specimen from damage.

Another object is to provide means for folding a specimen carrier in a predetermined manner and to lead the folded carrier into a container for holding the specimen secure for transport.

Another object is to provide a container for a slide carrier which together with the slide carrier provides flexible suspension for transporting a specimen.

Another object is to provide a telescopic slide carrier container which is of suitable length when extended to secure therein a specimen carrier ready for use and which has double side walls for protecting a specimen when telescoped to secure the carrier load with a specimen smear.

Another object is to provide a slide carrier container which has perforations for drying specimen fixative after the container is closed.

Another object is to provide a telescopic container for a slide carrier, which has two sections, one of which fits into the other section, wherein one of the sections has a scored detent which bears upon the other section when the sections are pressed toward one another.

Another object is to provide a folded specimen carrier for laboratory slides which has means for grasping the carrier to insert it into and remove it from a container without interfering with specimen applied to a slide.

Another object is to provide a laboratory test kit which is inexpensive and simple to manufacture and use and most efficient for expendient and safe handling of a laboratory specimen without contamination or damage to the specimen or its carrier.

Another object is to provide a method for preserving laboratory specimen which includes the steps described.

These and other advantages and objects of the invention will become more apparent as this description proceeds, taken in conjunction with the accompanying drawings.

BRIEF DESCRIPTION OF THE DRAWINGS

In the drawings:

FIG. 1 is a view of the closed container for the kit embodying the present invention, in extended unused condition.

FIG. 2 is a view similar to FIG. 1, except with the outer telescopic section removed.

FIG. 3 is a perspective view of the contents of the kit ready for taking a specimen.

FIG. 4 is a perspective view of the carrier tray with its legs bent in a direction reverse to that shown in FIG. 3.

FIG. 5 is a perspective view of the folded carrier tray at the point of insertion into the small section of the container.

FIG. 6 is an end view of the loaded smaller section after insertion of the carrier tray.

FIG. 7 is a view of the fully closed telescoped container ready for transport to the laboratory.

DESCRIPTION OF A PREFERRED EMBODIMENT

A laboratory test kit embodying the present invention, preferably comprises a telescopic container made up of a larger section 11 and a smaller section 12, each of which has a closed end 13, preferably with an aperture 14, for housing a slide carrier tray 15; and, preferably, an ampule 16 of fixative solution and utensils, such as a cervical scraper 17 and a swab applicator 18, which may be packed in a sterile envelop 19, are enclosed in the container.

Preferably, the slide carrier tray 15 comprises a pair of parallel spaced apart flaps or legs 20, and disposed therebetween is a slide receiving surface 21, upon which a transparent laboratory slide 22 is secured. Preferably, the slide has a specimen receiving surface 23 disposed toward the center of the carrier 15 and a writing surface 24, which may be treated to receive indicia, such as a patient's name and date and other information, and the surface of the tray beneath the specimen receiving surface 23 may be opaque to permit easy viewing of a specimen smear when applied to that surface 23. Intermediate the length of the legs 20, the area may be cut-out, as at 25, for a purpose to be described, and the central portion of the slide receiving surface 21 may have an ampule aperture 26, for holding the fixative ampule 16 upright, after its tube 27 is cut, ready to apply fixative solution to the slide specimen receiving surface 23. When the ampule 16 is removed from the aperture 26, the carrier tray 15 may be folded along the fold line 28, which has been weakened by the aperture 26.

The specimen S may be taken by means of the cervical scraper 17 or the applicator swab 18, which may be canted for easy grasping on the carrier tray 15, preferably with the specimen receiving surface 23 elevated in the manner shown in FIG. 3. Following the application of the specimen S, usually smeared on the surface 23, the fixative is applied from the tube 27 of the ampule 16 to the specimen S, whereupon the ampule is removed from its aperture 26 and the legs 20 are inverted, in the manner shown in FIG. 4, and the tray 15 is folded along the fold line 28, without damaging the specimen S by grasping the slide on the writing surface 24, in the manner shown in FIG. 5. The V-shaped cut-outs 25 form a leading edge 30 which allows for easy insertion of the folded carrier tray 15 into the open end 31 of the smaller telescopic tubular section 12 of the container.

When thus inserted into the section 12, as shown in FIG. 6, the legs 20 in sort of a "H-shaped" configuration bear against the wall of container 12, holding the slide 22 suspended in a position to ride flexibly in the container, resisting damage of the slide 22 and the specimen S applied thereto. The outer section 11 is pressed downwardly over the section 12, to contain the specimen S and its tray 15 for transport to the laboratory for examining thus protecting the carrier contents by the walls of both the tube sections 11 and 12.

The presence of the perforations or holes 14 not only permit quick escape of air to ease closing of the tube sections 11 and 12, but also they provide a means for allowing air to pass over the specimen S, so that one need not await full drying of the fixative before closing the container, as drying can be completed during transport without damaging the slide 22.

A label 35 may be applied to the outer surface of the larger section 11, which may consist of a laboratory requisition or mailing label, for directing delivery of the specimen to the laboratory. Also, the outer tube 11 may be provided with a stop score 36, which may be used for locating the extended position of the telescopic container, as shown in FIG. 1, or when place on the inner section for locating the closed position of the telescoped container.

Preferably, the written indicia is applied to the writing surface 24 of the slide 22, while the tray 15 is extended, as shown in FIG. 4. This writing surface 24 can be used for handling the folded tray 15 while it is being inserted into the tube section 12, as shown in FIG. 5, and removed therefrom, by grasping the writing surface between the thumb and index finger, without damaging the specimen.

Preferably, the container is tube-like to provide maximum strength to the container without use of special materials, and preferably the tube sections 11 and 12 and the tray are fabricated from cardboard. As seen in FIG. 6, a cylindrical configuration for the container is preferred because if the tubular sections 11 and 12 become out-of-round, the legs 20 of the tray 15 can conform to the shape of the sections without damaging the slide 22 or the specimen receiving area 21 of the carrier tray 15.

While the test kit and method embodying the present invention have been described for use in collecting gynecologic specimen, such as a Pap smear, substantially the same kit and method may be used in collecting specimen for venereal desease testing, for example in testing for Chlamydia, Herpes or Gonorrhea, except another fixative solution may be used and the microscope slide may have a special painted surface.

While a preferred embodiment of the kit and preferred steps of the method have been shown and described in considerable detail, many changes can be made in the structure and method steps without departing from the spirit or scope of the invention. It is not desired that the invention should be limited to the exact structure or process described.

I claim:

1. A laboratory test kit comprising a container, a slide carrier tray adapted for insertion into and removal from said container, said slide carrier tray including first, second, third, fourth, fifth and sixth sections, with at least one of said first and second sections having a slide receiving surface on one side thereof, a slide secured to said slide receiving surface, part of said slide being transparent and adapted for receiving a specimen thereon, said first and said second sections having a hinged connection to each other, with said first and second sections rotating about an arc of about at least 180 degrees about said connection, said first and second sections, at one end of said arc, lying in substantially the same plane and, at the other end of said arc, lying against each other, said third and fourth sections being connected to said first section and said fifth and sixth sections being connected to said third section, said third and fourth sections each having a perpendicular orientation relative to said first section and said fifth and sixth sections each having a perpendicular orientation relative to said second section such that when said first and second sections lie against each other, said first through sixth sections form an H, with said third through sixth sections forming the legs of said H and said first and seocnd sections forming the cross bar of said H, said third, fourth, fifth, and sixth sections being adapted to bear against said container when said tray forms said H.

2. The laboratory test kit of claim 1 wherein said first through sixth sections are formed integrally.

3. The carrier tray recited in claim 2 wherein said third through sixth sections have a V-shaped cut-out along said hinged connection of said first and second sections to each other.

4. The laboratory test kit of claim 1 further including means, located in proximity to said hinged connection, for holding an ampule of solution when said first and second sections lie in the same plane.

5. In the laboratory test kit recited in claim 1, wherein said container comprises tube sections, one section fitting within another tube section.

6. In the laboratory test kit recited in claim 5, wherein a tube section has a peripheral detent which indicates the position of one tube section relative to the other tube section when the sections are telescoped one over another section, said telescoped tube sections having a first extended position and a second collapsed condition.

7. In the laboratory test kit recited in claim 6, wherein said container telescopable sections which when in extended position hold said tray elongated for removal from said contained adapted for receiving a specimen applied to said slide, and when in collapsed position are adapted to receive said tray folded for protecting said slide and specimen within said container.

8. In the laboratory test kit recited in claim 1, wherein a perforated end wall permitting free flow of air closes said container.

9. The laboratory test kit package recited in claim 1, wherein said tray has means for holding said ampule upright ready for applying solution to said slide when opened.

10. The laboratory test kit package recited in claim 4, wherein said container has double walls defined by said telescoped sections projecting said slide when said tray is secured within one of said tubular sections.

11. The laboratory test kit package recited in claim 1, wherein said container and said carrier tray are fabricated from cardboard.

12. A slide carrier tray comprising first, second, third, fourth, fifth and sixth sections, with at least one of said first and second sections having a slide receiving surface on one side thereof, and a slide secured to said slide receiving surface, part of said slide being transparent and adapted for receiving a specimen thereon, said first and said second sections having a first hinged connection to each other, with said first and second sections rotating through a first arc of about at least 180 degrees about said first connection, said first and second sections, at one end of said first arc, lying in substantially the same plane and, at the other end of said first arc, lying against each other, said third and fourth sections having second and third hinged connections, respectively, to said first section with said third and fourth sections rotating through second and third arcs, respectively, of about 180 degrees about said second and third connections respectively and said fifth and sixth sections having fourth and fifth hinged connections, respectively to said third sections, with said fifth and sixth sections rotating through fourth and fifth arcs, respectively, about 180 degrees about said fourth and fifth connections, respectively, said third and fourth sections, when at one end of said second and third 180 degree arcs, respectively, each having a perpendicular orientation relative to said first section and, when at the other end of said second and third arcs, respectively, each having a perpendicular orientation relative to said first sections but lying in an opposite direction than when at said one end of said second and third arcs, and said fifth and sixth sections, when at one end of said fourth and fifth arcs, respectively, each having a perpendicular orientation relative to said second section and, when at the other end of said fourth and fifth arcs, respectively, each having a perpendicular orientation relative to said second section but lying in an opposite direction than when at said one end of said fourth and fifth arcs, such that when said first and second sections lie in the same plane and said third, fourth, fifth, and sixth sections lie at said one end of said second, third, fourth and fifth arcs, respectively, said third through sixth sections form support legs to support said slide receiving surface, and, when said first and second sections lie against each other and said third, fourth, fifth, and sixth sections lie at the other end of said second, third, fourth, and fifth arcs, respectively, said first through sixth sections form an H, with said third through sixth sections forming the legs of said H and said first and second sections forming the cross bar of said H.

13. The carrier tray of claim 12 wherein said first through sixth sections are formed integrally.

14. The carrier tray of claim 12 further including means, located in proximity to said hinge connection, for holding an ampule of solution when said first and second sections lie in the same plane.

15. The carrier tray recited in claim 12, wherein said tray has an aperture adapted for holding an ampule of solution upright therein.

16. The carrier tray recited in claim 12 wherein said said third through sixth sections are bendable to said other ends of said second through fifth arcs, respectively, towards said slide but out of contact with said specimen receiving surface.

17. The carrier tray recited in claim 16 wherein said tray is adapted for insertion into a tubular container when folded, and said third through sixth sections have a leading edge tapered from said slide receiving surface to a free end thereof for ease of inserting said folded tray into said tubular container.

18. The carrier tray recited in claim 17, wherein said tray is apertured midway its length to define a location for folding said tray.

19. The carrier tray recited in claim 18, wherein said score line thereacross intersects said aperture.

20. The carrier tray recited in claim 19, wherein said tubular container and said carrier tray are dimensioned to permit snug fitting of said tray when folded within said container.

21. The carrier tray recited in claim 20, wherein said tubular container and said carrier tray are dimensioned for said slide receiving surface to snugly span said container.

22. The carrier tray recited in claim 21, wherein said tubular container and said carrier tray are dimensioned for said third through sixth sections when rotated to the other end of said second through fifth arcs respectively to bear against said tubular container.

23. The carrier tray recited in claim 12, wherein the surface of said tray beneath said transparent part of said slide is opaque.

24. A method for securing and transporting a laboratory specimen comprising the steps of arranging on a foldable carrier tray having bendable legs a slide mounted for receiving a specimen and an ampule of solution for fixing said specimen on said slide, taking the specimen and smearing it on the slide, applying the fixative solution over the specimen, bending the legs and folding said tray to protect said specimen applied to said slide, inserting the tray into a container for transporting the specimen, said specimen being recessed on the folded tray and said legs being arranged to bear against said container securing said specimen from damage, and closing the container for transport to a laboratory.

25. The method recited in claim 24, wherein said ampule is secured on said tray and opened before the specimen is smeared on to said slide.

26. The method recited in claim 25, wherein said tray is elevated before said specimen is applied on to said slide.

27. The method recited in claim 24, wherein the source of said specimen is written on the edge of the slide before the tray is inserted into the container.

28. A method of inserting a slide carrier tray into a container comprising:
(A) rotating first and second sections of said tray about a hinged connection connecting said first and second sections, at least one of said first and second sections having a slide receiving surface on one side thereof, through a substantially 180 degree arc from a position where said first and second sections lie in the same plane to a position when said first and second sections lie against each other;
(b) rotating third and fourth sections, having hinged connections, to said first section to a perpendicular orientation relative to said first section and fifth and sixth sections, having hinged connections to said second sections, to an orientation perpendicular to said second sections such that when said first and second sections lie against each other, said first through sixth sections form an H with said first and second sections forming the cross bar of said H; and
(C) inserting said slide carrier tray with said first through sixth sections forming an H into a container with said third through sixth sections bearing against the inside surface of said container.

* * * * *